US010350008B2

(12) United States Patent
Gibbs et al.

(10) Patent No.: US 10,350,008 B2
(45) Date of Patent: Jul. 16, 2019

(54) VISUAL GUIDANCE DISPLAY FOR SURGICAL PROCEDURE

(71) Applicant: X-Nav Technologies, LLC, Lansdale, PA (US)

(72) Inventors: Jason Gibbs, State College, PA (US); Scott A. Merritt, Green Lane, PA (US); Edward J. Marandola, Gwynedd, PA (US); Christopher W. Scharff, Collegeville, PA (US); Glenn A. Straub, Douglassville, PA (US); Robert W. Emery, III, Mclean, VA (US)

(73) Assignee: X-Nav Technologies, LLC, Lansdale, PA (US)

( * ) Notice: Subject to any disclaimer, the term of this patent is extended or adjusted under 35 U.S.C. 154(b) by 1261 days.

(21) Appl. No.: 14/558,255

(22) Filed: Dec. 2, 2014

(65) Prior Publication Data
US 2016/0151117 A1    Jun. 2, 2016

(51) Int. Cl.
*A61B 19/00* (2006.01)
*A61B 17/17* (2006.01)
(Continued)

(52) U.S. Cl.
CPC ........ *A61B 19/5244* (2013.01); *A61B 5/4893* (2013.01); *A61B 5/7405* (2013.01);
(Continued)

(58) Field of Classification Search
CPC ....... A61B 34/20; A61B 34/25; A61B 5/4893; A61B 5/7405
See application file for complete search history.

(56) References Cited

U.S. PATENT DOCUMENTS

2005/0085714 A1    4/2005 Foley et al.
2007/0073136 A1    3/2007 Metzger
(Continued)

FOREIGN PATENT DOCUMENTS

| EP | 1571581 A1 | 9/2005 |
| WO | 2012109760 A1 | 8/2012 |
| WO | WO2015048994 A1 | 4/2015 |

OTHER PUBLICATIONS

Extended European Search Report dated May 17, 2016 (EP Appl. No. 15196433.5).

*Primary Examiner* — Joseph M Santos Rodriguez
(74) *Attorney, Agent, or Firm* — Drinker Biddle & Reath LLP

(57) ABSTRACT

A visual guidance system for use in a surgical procedure. The system includes an image processing unit programmed to receive a three-dimensional image of a surgical area, information on an instrument being used in the procedure, and a surgical plan including a planned trajectory that the instrument should follow. The image processing unit generates a derived representation of the surgical procedure depicting the movement of the instrument on the three-dimensional image. A graphical guidance indicator is disposed on the three-dimensional image with a center point of the graphical guidance indicator centered on the planned trajectory, the graphical guidance indicator being displayed orthogonal to the planned trajectory. The derived image and the graphical guidance indicator depict at least five degrees of freedom of motion of the instrument. The graphical guidance indicator is changed based on the movement of the instrument in accordance with the surgical plan.

48 Claims, 13 Drawing Sheets

(51) Int. Cl.
  *A61B 5/00* (2006.01)
  *A61C 1/08* (2006.01)
  *A61C 3/02* (2006.01)
  *A61C 8/00* (2006.01)
  *A61B 34/00* (2016.01)
  *A61B 34/20* (2016.01)
  *A61B 34/10* (2016.01)

(52) U.S. Cl.
  CPC .......... *A61B 17/1703* (2013.01); *A61B 19/50* (2013.01); *A61B 19/56* (2013.01); *A61B 34/20* (2016.02); *A61B 34/25* (2016.02); *A61C 1/084* (2013.01); *A61C 3/02* (2013.01); *A61C 8/0089* (2013.01); *A61B 2019/505* (2013.01); *A61B 2019/507* (2013.01); *A61B 2019/508* (2013.01); *A61B 2019/524* (2013.01); *A61B 2019/5265* (2013.01); *A61B 2019/562* (2013.01); *A61B 2019/564* (2013.01); *A61B 2034/107* (2016.02); *A61B 2034/2055* (2016.02); *A61B 2034/256* (2016.02)

(56) References Cited

U.S. PATENT DOCUMENTS

| | | |
|---|---|---|
| 2008/0039717 A1 | 2/2008 | Frigg et al. |
| 2011/0237935 A1 | 9/2011 | Kalpin et al. |
| 2014/0147807 A1 | 5/2014 | Yau et al. |

# VISUAL GUIDANCE DISPLAY FOR SURGICAL PROCEDURE

FIELD OF THE INVENTION

The present invention relates to a surgical procedure and, more particularly, to a visual display system for providing a consolidated view in real-time of a surgical procedure with guidance to a surgical plan.

BACKGROUND

There have been significant strides in surgical navigation systems in recent years. The current systems provide visualization of a surgical site on a computer monitor. Conventional systems operate by first creating a high-resolution three dimensional image of the anatomical region of interest. In dentistry, the preferred imaging modality is cone beam computed tomography, referred to herein as the "CT."

Using the image of the anatomical region, the surgeon creates a pre-operative plan in the area of operation identifying the desired location, depth and orientation of an implant on the CT image.

During the operative procedure, a software system including tracking software, aligns or adjusts the position of the patient's jaw as observed in the operating suite with the pre-operative plan that is stored on the computer system. The system then detects the surgical tool (drill) and determines the location and orientation of the surgical tool with respect to the patient and the pre-operative plan. This information is then depicted on the screen as a representation.

Using this information, in order to place an implant in a jaw, the surgeon will follow these steps:

Find the position in the patient's jaw where the hole should be drilled into the bone.

Place the drill tip in the proper position at the desired location, rotate the drill about the tip to the position the drill at the correct angular orientation.

Drill into the tooth or bone, counteracting the drill's tendency to deviate from the desired trajectory as the bit twists into the bone.

Continue along the planned trajectory until the drill tip is at the pre-planned depth within the bone.

Failure to appropriately place the implant in the pre-planned location can result in a suboptimal aesthetic outcome or may injure the patient if the implant impinges on a nerve or erupts into surrounding anatomy if driven too deeply or in the wrong location.

Because the surgeon is concerned with correct placement in three dimensions, most state of the art navigation systems simultaneously depict the instantaneous location of the surgical instrument with respect to the patient's anatomy from several different viewpoints. Referring to FIG. 1, a display from conventional navigation systems is shown. The display 10 includes a panoramic view 10, typically of the entire jaw or at least the upper or lower jaw portion captured in an earlier scan. On the panoramic the current position of the drill 11 is represented as well as the depiction of the planned implant 12. A live camera view 13 of the operating suite may be included. A computer generated comparative view 14 is displayed visually depicting the current displacement in buccal/lingual and mesial/distal directions of the drill 11 with respect to the planned implant 12. A computer generated comparative view 15 is displayed visually depicting the current displacement of the angular orientation of the drill 11 with respect to the planned implant 12 along its long axis.

FIG. 1 also includes a front view 16 and a side view 17 of the prior CT scans with the planned implant 12 and the current drill tip location 11 illustrated. These views also include a depiction of a nerve 18 in close proximity. The long axis 19 of the planned implant is illustrated depicting the positional misalignment in each plane. These views permit the surgeon to see a visual depiction of the current depth of the drill tip 11.

While conventional systems provide a combination of images that unambiguously show the orientation, depth and trajectory of a surgical instrument inside the patient with respect to a planned implant location, the multiple views that the surgeon must constantly comprehend can be exhausting to the surgeon. The surgeon must constantly shift focus between the different views, ensuring that every movement made to correct a deviation in one view does not adversely introduce error that can only be detected in a different view. These shifts in focus lead to user strain and can potentially lead to suboptimal outcomes.

A need exists for an improved guidance system that depicts in real time the position and orientation of the surgical tool with respect to the patient's body and the planned implant trajectory. As a hole is drilled for the implant or as the implant is delivered into the bone, the system should clearly indicate if the surgeon is deviating from the planned trajectory in such a manner as to allow for straightforward correction. Additionally, upon the drill reaching the planned location within the body, the event should be readily apparent to the surgeon so further drilling can be stopped. The surgeon is trying to continuously maintain a proper position in the jaw with alignment to the planned trajectory all while drilling to the correct depth. It is therefore desirable that all the pertinent information is presented in a manner appropriate for simultaneous consumption by the surgeon. The current state of the art navigation systems fail to meet these basic objectives.

SUMMARY OF THE INVENTION

The present invention is directed to a visual guidance system for use in a surgical procedure. The guidance system displays a derived image of the surgical procedure on a display. The guidance system includes a detection system or program for detecting and tracking a position and orientation of an instrument and tracking the position and orientation of a portion of a patient. The detection system registers the position and orientation of the portion of the patient to a prestored three-dimensional image of a portion of the patient. The detection system determines the location and orientation of an operating axis of the instrument relative to the prestored three-dimensional image.

A display is provided for displaying the derived image of the surgical procedure.

An image processing unit is included which is programmed to receive the prestored three-dimensional image, the instrument location and orientation, and a predetermined surgical plan including data representing a desired surgical result using the instrument for depiction on the prestored three-dimensional image and a planned trajectory to achieve the result.

The image processing unit is programmed to generate a derived image of the surgical procedure including a three-dimensional visual representation of a portion of the instrument on the prestored three-dimensional image based on the location and orientation of the operating axis relative to a longitudinal axis of the planned trajectory. The derived image also includes a depiction of the planned trajectory on the prestored three-dimensional image. The derived image is formed orthogonal to the planned trajectory.

The image processing unit is programmed to generate a graphical guidance indicator on the image display apparatus. The graphical guidance indicator is oriented so as to be depicted orthogonal to the planned trajectory.

The image processing unit also sends the derived image to the display. The derived image and the graphical guidance indicator providing a visual depiction of at least five degrees of freedom of motion of the instrument relative to the surgical plan.

The image processing unit changes the depiction of the graphical guidance indicator on the display based on the movement of the instrument in accordance with the surgical plan.

In an embodiment, the surgical result is a drilled hole with a final depth. The surgical plan is a three-dimensional representation of the drilled hole. The system permits a user to select the three dimensional drilled hole shape.

In one embodiment, the instrument is a drill with a drill bit, and the operating axis is a longitudinal axis of the drill bit. In this embodiment, the surgical procedure is an oral surgical procedure which involves drilling into bone of a tooth.

The representation of the drill may include an annular cylindrical outer housing of a drill head and a concentric substantially cylindrical representation of a drill bit located within and spaced apart from the outer housing.

In an embodiment, the graphical guidance indicator includes an aiming ring disposed around and centered on a longitudinal axis of the planned trajectory. The aiming ring provides a visual guide for a surgeon to use to locate the representation of the drill bit on the longitudinal axis of the planned trajectory.

The graphical guidance indicator optionally includes an X mark centered on the longitudinal axis of the planned trajectory. The orientation of the X mark is associated with the orientation of the prestored three-dimensional image.

The graphical guidance indicator may include a reticle centered on the longitudinal axis of the planned trajectory. The reticle provides a horizontal and vertical reference point relative to the image display. The reticle may include spaced apart tick marks representing distance relative to the prestored three-dimensional image. As such, the image processing unit may be programmed to adjust the spacing of the tick marks on the image display depending on a zoom level of the display of the prestored three-dimensional image.

In one embodiment, the graphical guidance indicator includes a targeting ring disposed around and centered on the longitudinal axis of the planned trajectory. The targeting ring is preferably concentric with and located around the aiming ring. The targeting ring provides a visual guide for a surgeon to use to locate the representation of the drill head, so as to align the drill head with the longitudinal axis of the planned trajectory.

It is contemplated that the image processing unit may receive data representing the location of a nerve in the prestored three-dimensional image. The image processing unit may depict a representation of the location of the nerve relative to the prestored three-dimensional image on the derived image.

In an embodiment, the graphical guidance indicator includes a depth indicator adjacent to the targeting ring. The depth indicator is configured to be adjusted based on the movement of the drill bit along the planned trajectory. The depth indicator may be formed as a portion of a ring having a center coincident with the center of the targeting ring. The image processing unit changes the depth indicator by depicting a larger portion of the ring correlated to the depth of the drill bit in relation to a planned drilling depth. Alternately or in addition, the image processing unit can visually change the shading or coloring of the depth indicator on the image display based on the depth of the drill bit in relation to a planned drilling depth.

In the event that the surgical plan involves different diameter drill bits, it is contemplated that the graphical guidance indicator can be visually changed to indicate when a different drill bit is required. For example, the aiming ring can be automatically resized to a diameter to accommodate the new drill diameter.

It is also contemplated that the image processing unit can provide audible signals as the drill bit progresses along the planned trajectory toward the desired drilling depth.

A method is also disclosed for providing visual guidance for a surgical instrument during a surgical procedure.

The foregoing and other features of the invention and advantages of the present invention will become more apparent in light of the following detailed description of the preferred embodiments, as illustrated in the accompanying figures. As will be realized, the invention is capable of modifications in various respects, all without departing from the invention. Accordingly, the drawings and the description are to be regarded as illustrative in nature, and not as restrictive.

BRIEF DESCRIPTION OF THE DRAWINGS

For the purpose of illustrating the invention, the drawings show a form of the invention which is presently preferred. However, it should be understood that this invention is not limited to the precise arrangements and instrumentalities shown in the drawings.

DETAILED DESCRIPTION OF THE PREFERRED EMBODIMENTS

Figure 1:
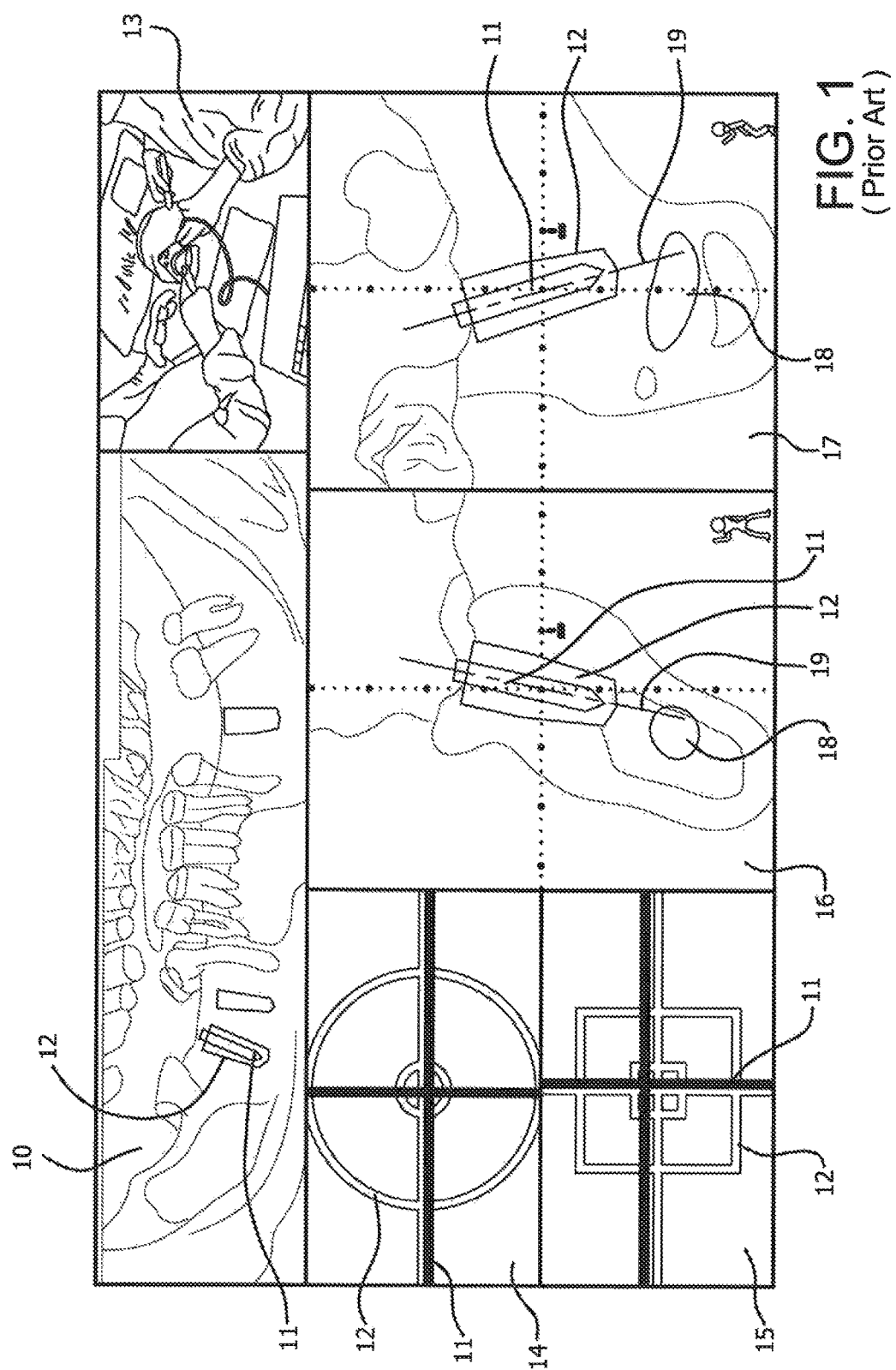
FIG. 1 illustrates a prior art computer display for monitoring and tracking a surgical procedure.
Figure 2:
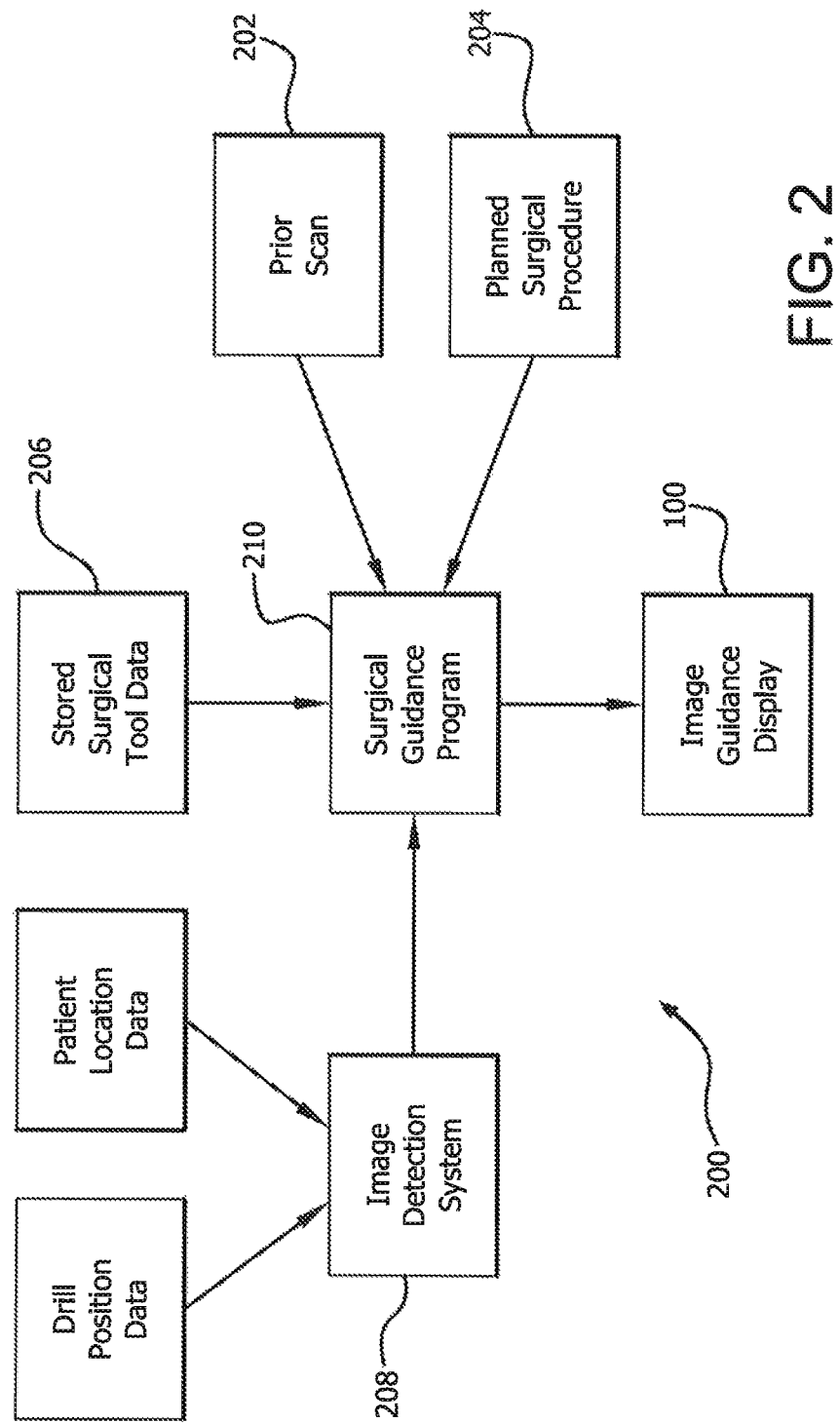
FIG. 2 is a schematic representation of a system according to the present invention for displaying and tracking a surgical procedure.

Referring to FIGS. 2-10, an embodiment of the present invention is depicted for providing a method and system for visually displaying an image guided surgical procedure. While the procedure depicted in the images is a dental procedure, it should be readily apparent that the system and method could be applied to any number of different surgical procedures where the insertion of a probe, needle, or treatment device to a specific location and depth inside the body, for example tumor biopsies and orthopedic device placement.

One dental procedure that would benefit from precise guidance is the placement of dental implants within the jaw. The present system assists in (i) locating and depicting the correct location of the drill tip entry into the bone, (ii) depicting the direction and orientation of the drill tip, and (iii) providing information on the position of the drill tip within the anatomy even when not directly visible. If the drill tip's entry point aligns with the planned procedure and the drill is delivered into the bone in the proper trajectory, the third objective reduces to knowing the precise depth of the drill into the bone.

To address the shortcomings of current surgical guidance systems, the inventors have developed a visual display and system that presents all the information required to align a surgical instrument in a precise location and orientation and then deliver it to a precise position within the patient according to a predetermined plan (e.g., following a preset trajectory.)

The display 100 provides a continuously updated rendering of three-dimensional objects in the surgical area of interest with an overlay of a graphical guidance indicator 102 and a three-dimensional depiction of the surgical tool (e.g., drill) 104. The vantage point of the three dimensional image scene 100 is chosen such that the virtual camera's image plane is perpendicular to the longitudinal axis of the preplanned hole that is to be drilled. As will become readily apparent, the present invention can work with any procedure where a planned trajectory or longitudinal axis is known. The planned trajectory is a surgical path that the instrument is to take to reach the planned end result (the final location). While in the illustrated embodiment the planned trajectory or surgical path is shown as a linear longitudinal axis, it should be readily apparent that, depending on the surgical procedure being undertaken, the trajectory could be a complex trajectory involving the use of multiple instruments, having different shapes, sizes and capabilities. The system is preferably designed such that the scene (displayed image) 100 may be panned, zoomed and rotated, but the orientation of the virtual camera (user's viewpoint) is maintained such that the image plane is perpendicular or orthogonal to the planned longitudinal axis (the planned trajectory). This permits straightforward drilling of the implant hole. If this perpendicular or orthogonal view were not used, a circle at the tip of the implant hole would appear elliptical, confounding efforts to align the drill tip along the implant hole's longitudinal axis.

There are several objects and depictions in the guidance view scene 100. A surgical plan is incorporated into the guidance indicators 102 and is depicted on the teeth/bones in the illustrated embodiment. To do this, the system 200 first requires that the surgeon create or input the surgical plan, including a planned implant location on the prior CT scan 202 of the surgical area. The surgical plan or implant location (which ego includes the location relative to the tooth/bone and the depth into the tooth/bone) is stored as a three dimensional representation 204, preferably as a 3D polygonal mesh that is overlaid on the CT scan. The system 200 may include software drawing tools which permit the surgeon to draw a 3D representation of the planned hole to be drilled. Alternatively, the system may include stored 3D mesh representations of predetermined implant hole configurations. The surgeon can then select the desired 3D hole representation. It is also contemplated that the surgeon could select the desired implant and the system could automatically select one or more 3D mesh representations that would be needed to create a hole suitable for the implant selected. The mesh representation is preferably stored separately from the prior CT scan. The surgical plan includes a trajectory (for example, a longitudinal axis) of the planned implant hole.

Also in this scene 100 is a computer generated representation of the drill 104 being used. The system 200 may include a database 206 of stored data representing multiple drills and drill bits. Based on the particular drill and drill bit being used (which can be inputted by the personnel at the time of the surgical procedure or could be automatically detected by the system, such as by optically detecting a code (e.g., bar or 2D graphical code) on the surgical tool or by detecting an RFID chip in the tool), the system 200 selects the appropriate graphical representation of the surgical drill and depicts it in the visual display 100. In the illustrated embodiment, the drill may be depicted as a hand piece 106 with a cored-out head 108 and a drill bit 110 of a specific length and diameter. The drill bit's 110 representation reflects the physical characteristics of the drill bit that is currently attached to the drill. As mentioned, this data may be extracted from the database 206. The data also includes an operating axis (which for a drill bit would be its longitudinal or drilling axis). During the course of the operation, the surgeon may use several drill bits to form the implant hole. By correctly depicting the drill bit length and diameter, the system permits accurate depiction of the drill depth into the jaw bone. By utilizing an image guidance or tracking system, such as the optical image guidance system developed by X-Nav Technologies, LLC and described in pending U.S. patent application Ser. Nos. 14/487,987, and 14/488,004, the disclosures of which are incorporated herein by reference in their entireties, the present invention can provide continuous real time data 208 representing the drill's position and orientation and the detected location of the surgical area, such as the location of the jaw bone. Those skilled in the art would readily appreciate that other guidance or tracking systems can be used, including electromagnetic tracking systems or mechanical arm encoding systems. The real time data 208 is used to accurately align the prior CT scan of the surgical area to the current surgical area. All the relevant data used by a computer program 210 that converts the data into representative images which are depicted the display 100. While the preferred embodiment uses a tracker that determines a full 6 degrees-of-freedom rigid-body transform for the surgical tool, it is possible to use a 5 degrees-of-freedom tracker instead, providing only the tool's X, Y, Z location along with the tool's axis.

Figure 3:
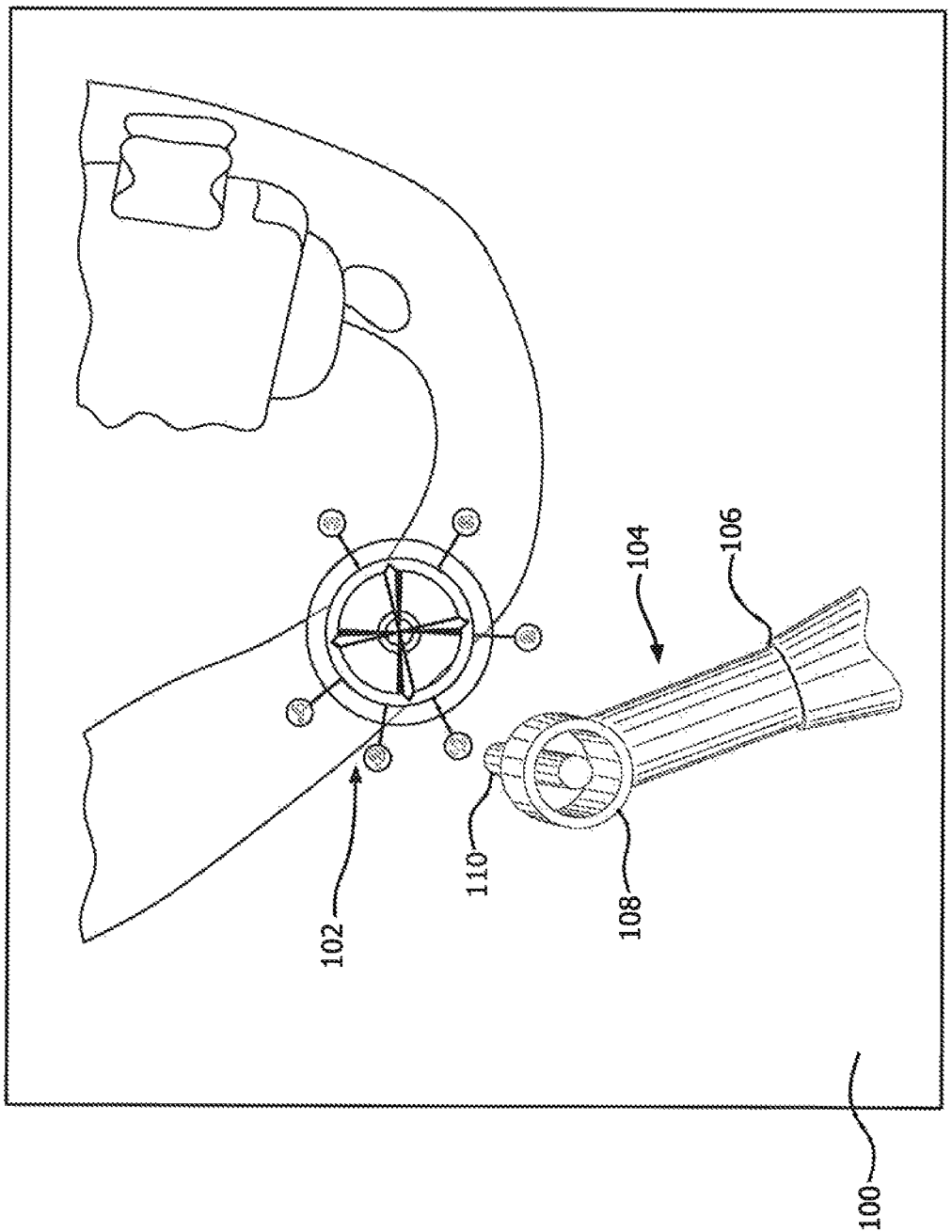
FIG. 3 is an illustration of a computer generated display for monitoring and tracking a surgical procedure according to the present invention.
Figure 4:
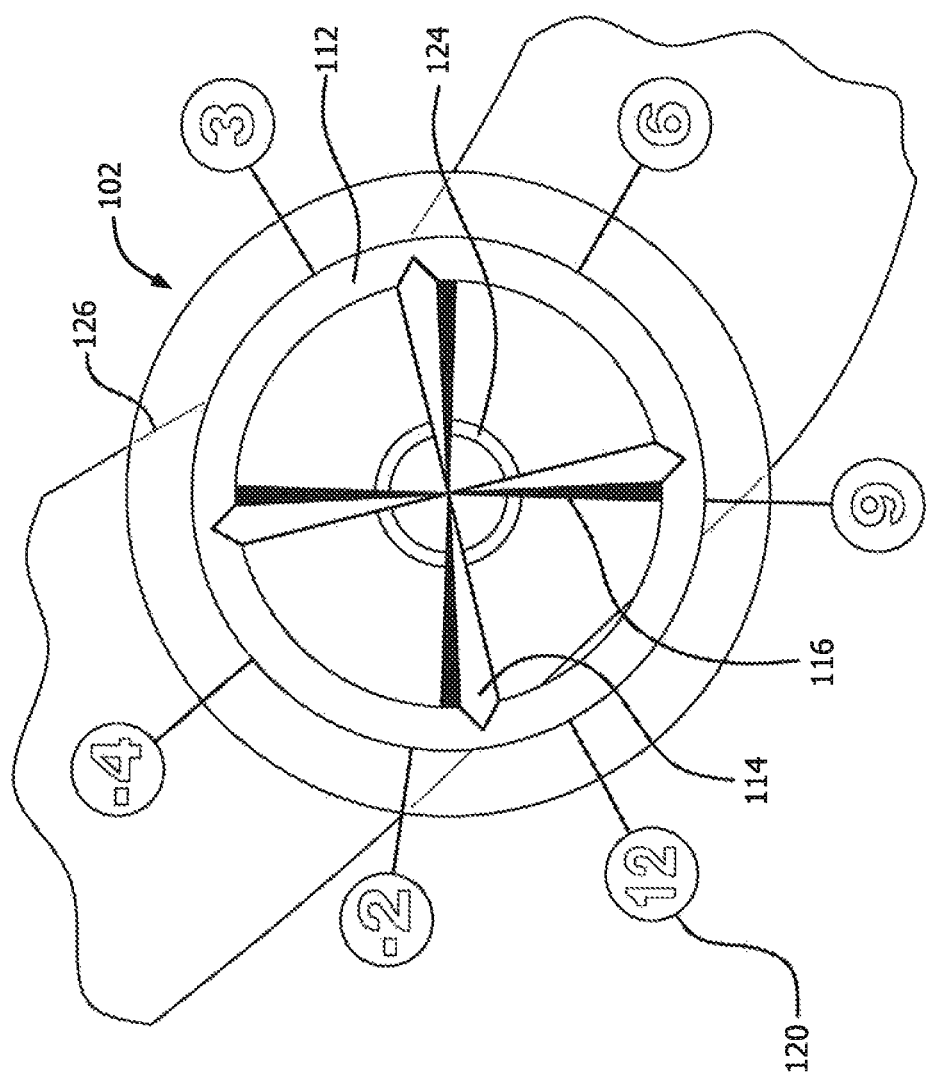
FIG. 4 is an enlarged illustration of a graphical interface used in the display of FIG. 3.
Figure 5:
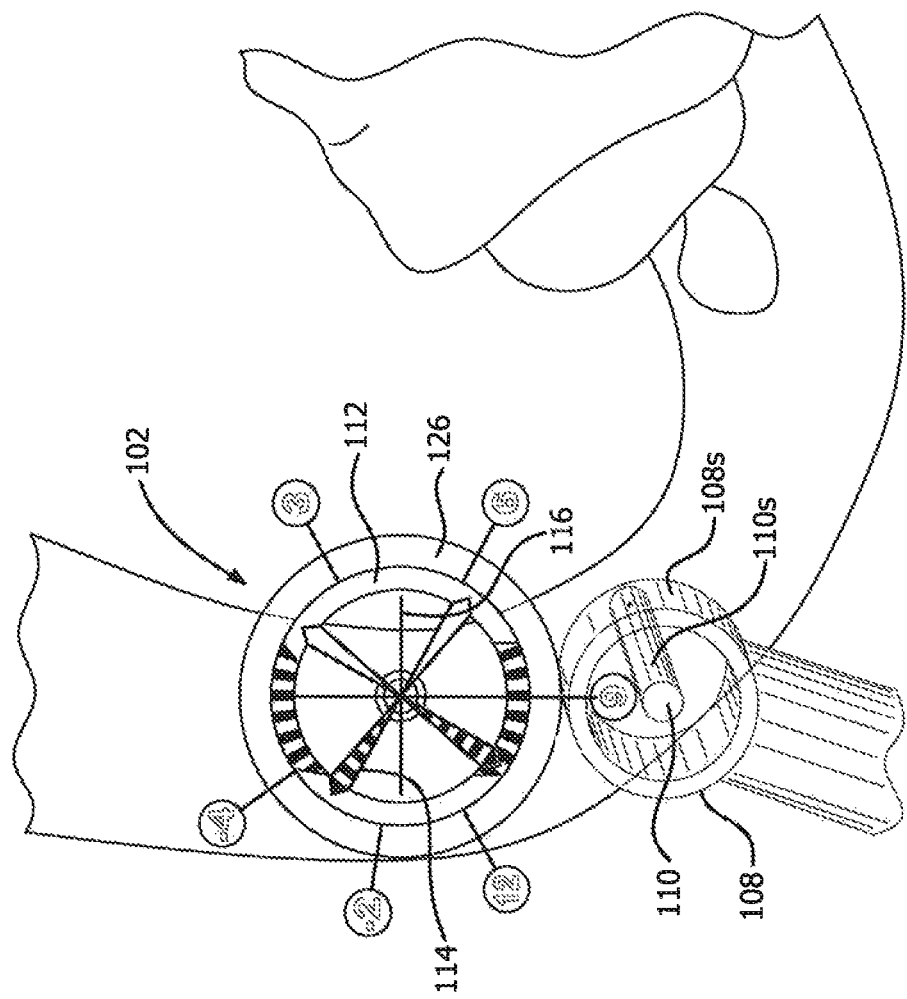
FIG. 5 is an illustration of the graphical interface of FIG. 4 with a portion of a representation of a surgical tool shown approaching a target site.
Figure 6:
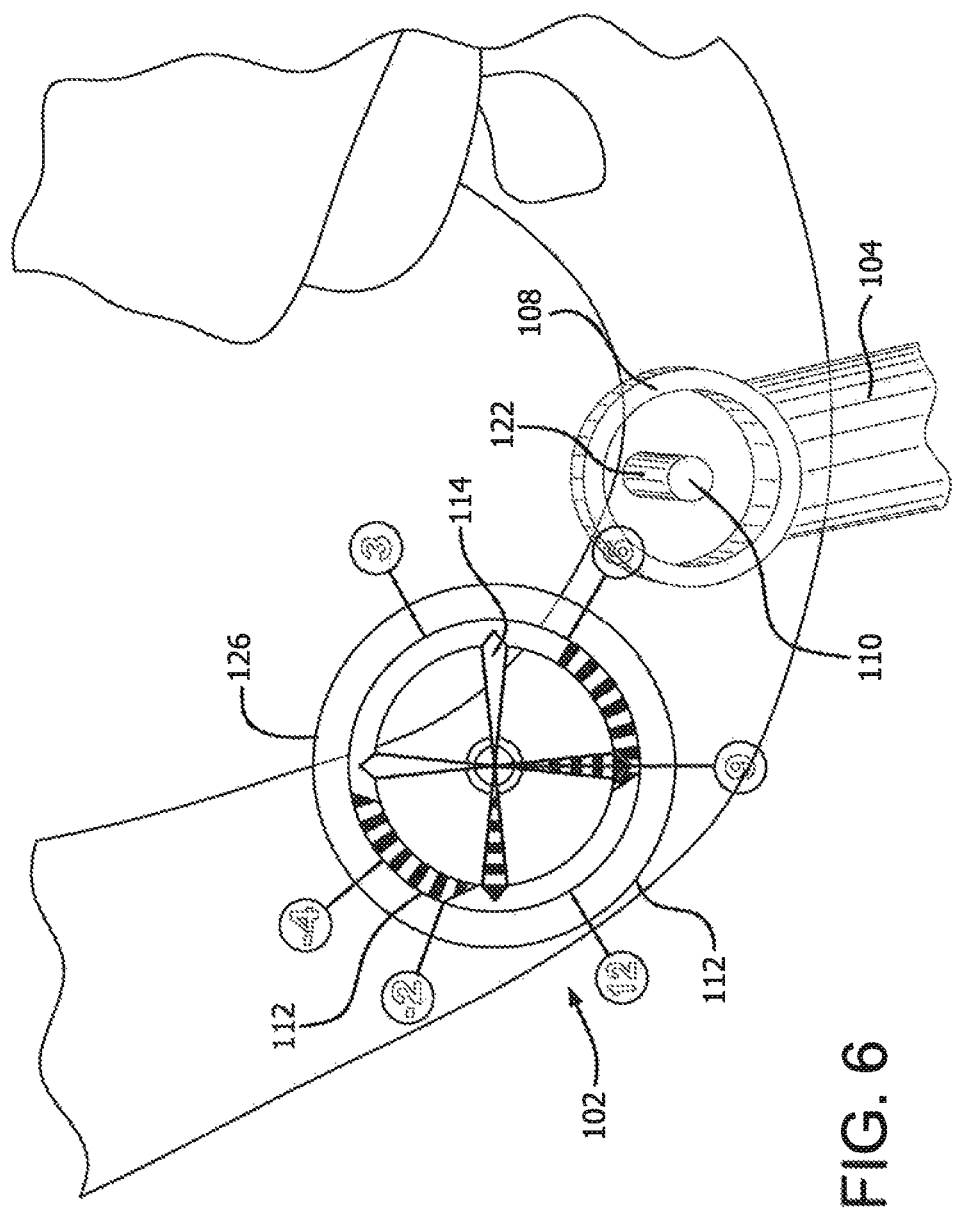
FIG. 6 is another illustration of the graphical interface of FIG. 4 with a portion of a surgical tool shown.

Referring to FIGS. 3 and 4, the system 200 preferably controls features of the display 100 by tracking the movement of the drill 104 and the movement of the patient for adjusting the location of the planned implant hole. As the drill 104 is detected entering the general surgical area, the system 200 depicts the representation of the drill 104, the trajectory and, optionally, the planned implant hole, on the display relative to the prior CT scan. The planned trajectory is surrounded by several visual cues or indicators that are configured to provide relevant information to the surgeon regarding the location, orientation and depth of the drill bit relative to the planned implant hole. As described below, these are all included in one combined active graphical guidance indicator 102.

As the surgical tool is brought toward the drilling location, the initial objective is to locate the drill tip 108 at the drilling location, which is depicted by an intermediate targeting ring 112 (which may be a certain color or shading, such as blue). The targeting ring 112 optionally surrounds cross-hairs 114, generally forming an "X" or "+" in the illustrated embodiment (i.e., an X mark). The graphical guidance indicator 102 may also include a fixed reticle 116 with a center collocated on the planned trajectory or longitudinal axis of the planned implant hole. The reticle 116 provides a horizontal and vertical reference point with respect to the screen. Thus, it does not rotate as the image is rotated. Compare FIGS. 5 and 6. The X mark 114, on the other hand, it tied to the scanned image and, while also centered on the planned trajectory or longitudinal axis of the planned implant hole, it will rotate relative to the reticle 116. The ability to depict the rotation of the X mark 114 relative to the reticle 116 provides a visual sense of rotary motion. The reticle 116 may include tick marks 117 (shown in FIG. 7) that are set to depict a prescribed distance, for example 1 mm. This gives the surgeon a sense of scale regardless of the zoom level of the system (i.e., the spacing of the tick marks 117 would change as the zoom level is changed. The level of accuracy required in certain procedures is a decision made by the surgeon and, therefore, providing this extra degree of visual information makes procedural decisions more accurate. The graphical guidance indicator 102 optionally includes numerical indicators 120 positioned around the targeting ring 112.

As discussed above, the scene is rendered in an orthographic projection, with the viewing plan being perpendicular to the planned trajectory or longitudinal axis of the planned implant hole. In such a rendering, the relative size of objects remains constant, regardless of their distance to the camera. This is in contrast to more conventional perspective projection, where closer objects appear larger. In the guidance view, the relative movements are quite small, so the depth cues that perspective projection provide minimal benefit and only serve to overwhelm the scene when it is close to the rendering camera (such as at the beginning of a surgical procedure where the drill could potentially fill the entire field of view.

It is also contemplated that the system would permit the surgeon to adjust the view, such as by rotation, to allow the view to be similar to the way the surgeon is viewing the actual jaw. The X mark 114 depicts the precise location where the hole should be drilled. Thus, the X mark 114 is fixed with respect to the jaw/bone/tooth, even when the view is rotated (i.e., the X mark will rotate with the rotation of the image of the jaw, or the movement of the patient in the view). The present invention permits the X mark 114 to be oriented with 6 degrees of motion in order to accommodate implants that are not rotationally symmetric. The X mark 114 and surrounding targeting ring 112 provide visual cues regarding the planned implant hole location with respect to the surrounding jaw structure. When situated above the jaw, these indicators are rendered in a solid, opaque coloring. When parts of the X mark 114 or targeting ring 112 are located below the bone, the portion of those visual indicators is rendered as a semi-transparent or dashed element, thus providing the visual suggestion of depth when looking down. See, for example, FIG. 6. This would occur if the starting point for the planned implant hole is located below the surface in the CT scan, for example if a portion of the bone or a gum line must first be removed before commencing the planned hole drilling.

As the surgical tool 104 gets closer to the surgical site (the planned implant hole) 102, the system allows the view to be zoomed in. This can either be performed by the user selecting a zoom in/out feature, or could happen automatically, for example, based on the distance that the drill head 108 is from the surgical site 102. As shown in the figures, the drill 104 and drill bit 110 are preferably drawn semi-transparent (translucent) so that the anatomy of the patient beneath the drill 104 and drill bit 110 can always be seen. It is contemplated that only the drill head 108 and drill bit 110 would be semi-transparent with the remainder of the surgical tool being opaque. Preferably, a small diameter or dot is depicted as tip 122 of the drill bit 110. In one embodiment, the tip 122 has a diameter of about 0.35 mm. This assists the surgeon by providing a guide for the surgeon to place on the center of the X mark and the reticle 116 (i.e., on the planned trajectory), thereby aligning the drill tip 122 with the center of the planned implant hole.

There are several visual cues or indicators that are part of the illustrated guidance indicator 102 and which facilitate the alignment of the drill bit 110 along the correct trajectory of the planned implant hole. The drill head 108 has a cylindrical outer diameter that is sized to fit within the inner diameter of the targeting ring 112. This provides the surgeon with an initial goal for the correct placement of the drill head 108. The guidance indicator 102 also preferably including an aiming ring 124 having a center coincident with the center of the reticle and the center of the targeting ring 112 such that the aiming ring 124 is concentric with the targeting ring 112. The aiming ring 124 has an inner diameter that is preferably sized such that the outer diameter of the drill bit 110 fits within the inner diameter of the aiming ring 124 when they are properly aligned. As will become apparent, this permits alignment of the drill head 108 and the drill bit 110 with the planned trajectory and the planned implant hole being drilled. This provides a visual guide for a surgeon to use to locate the representation of the drill bit on the planned trajectory. In an alternate embodiment, the aiming ring 124 is depicted with a size and shape corresponding to the shape of the three-dimensional planned hole orthogonal to the longitudinal axis. Thus, the drill bit in this embodiment would be smaller than the depicted aiming ring 124.

Figure 7:
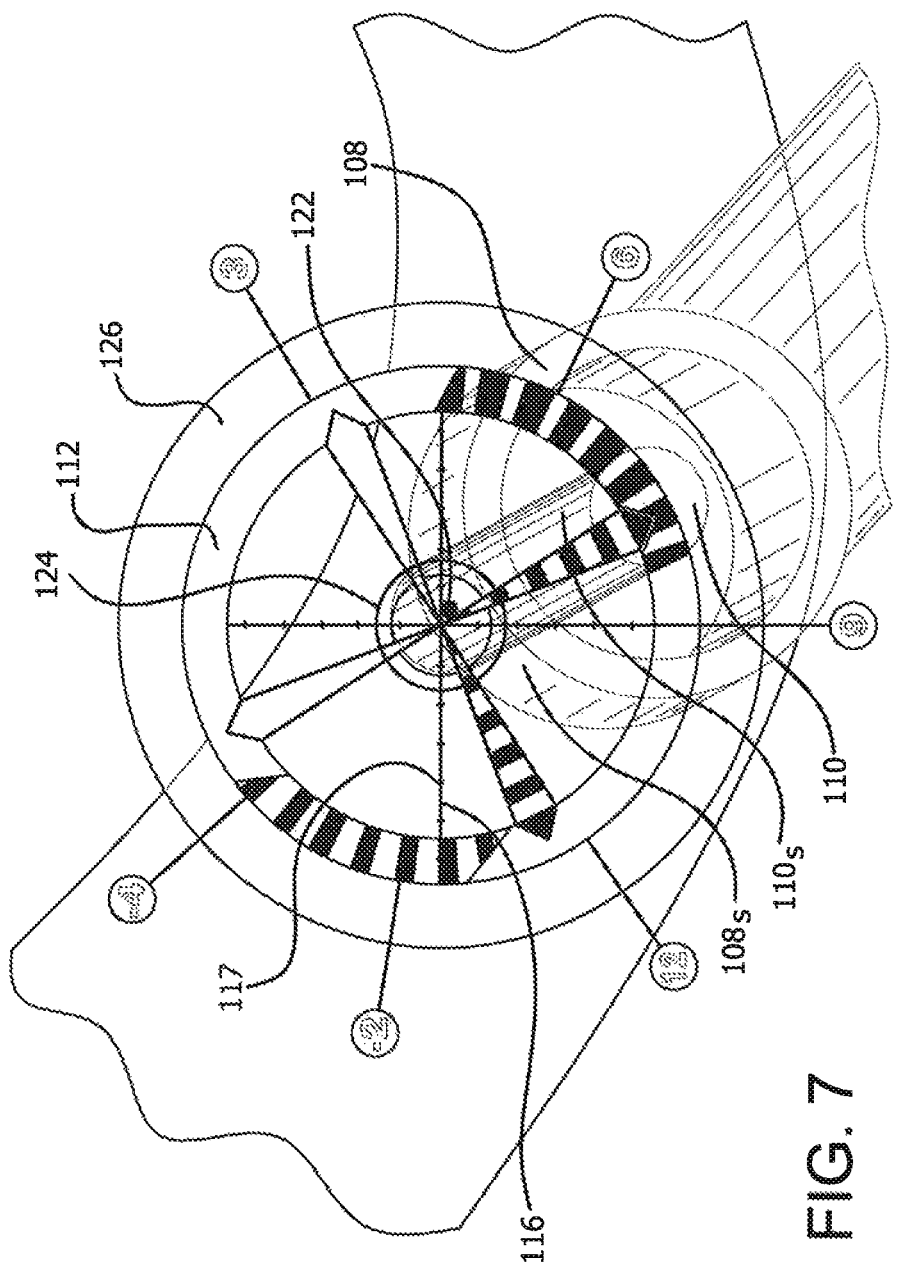
FIG. 7 is an enlarged illustration of the graphical interface of FIG. 6 with the portion of a surgical tool shown close to the target site.
Figure 8:
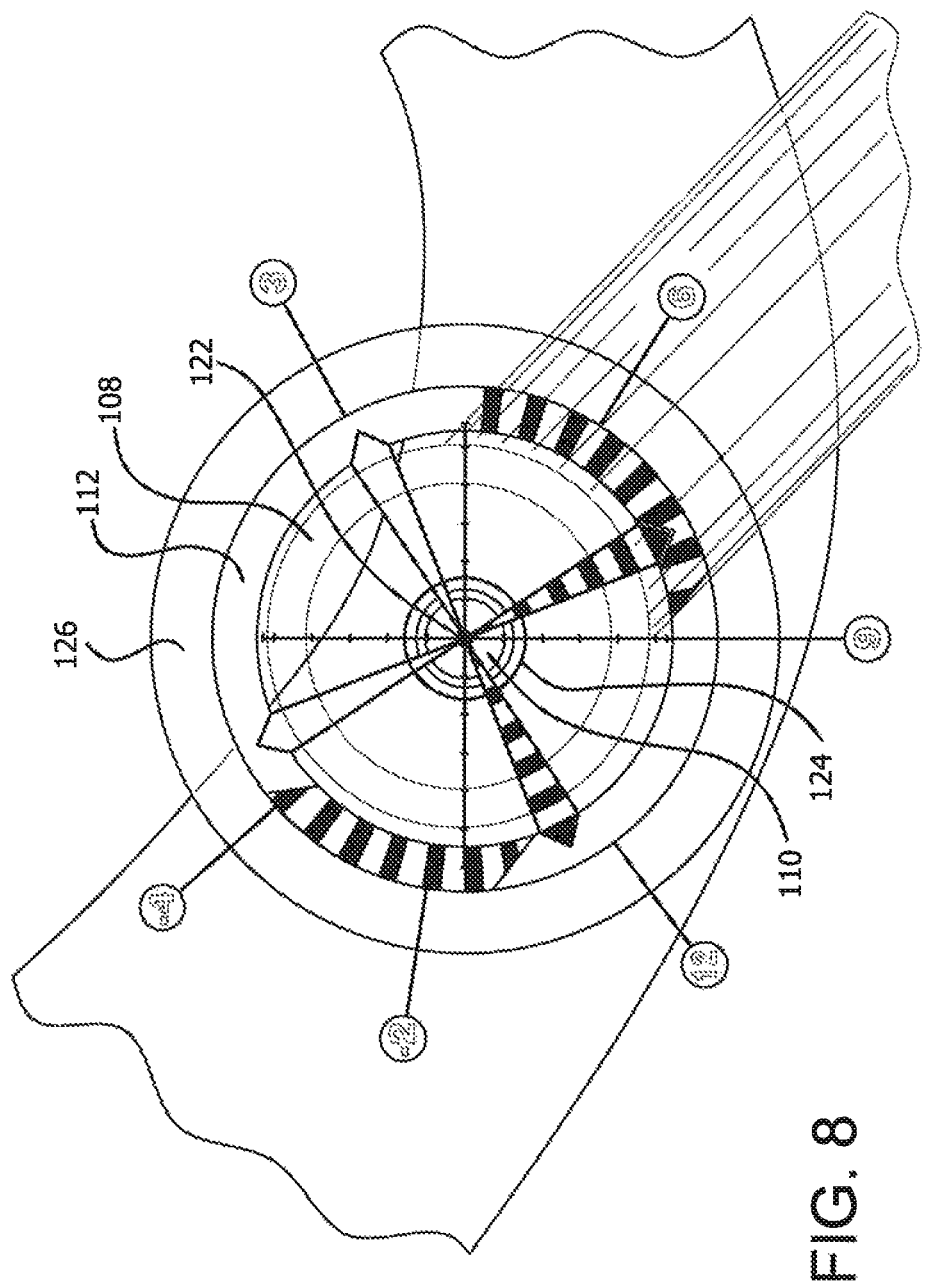
FIG. 8 illustrates the graphical interface of FIG. 7 with the surgical tool aligned on a planned drilling site.

Referring to FIG. 7, the surgeon moves the drill head 108 toward the targeting ring 112. As shown, the shaded portion of the drill head 108 depicts the sidewall $108_S$ of the drill head. Similarly, the shaded portion of the drill bit 110 depicts the sidewall $110_S$ of the drill bit. Since the view in FIG. 7 is set to be an orthogonal view looking directly down on the drill head 108, the sidewalls $108_S$ $110_S$ of the drill head and drill bit should not be visible in that view if the drill head 108 is properly oriented with the drill bit's longitudinal axis lying along the axis of the hole being drilled (i.e., the planned trajectory). Thus, the view in FIG. 7 quickly informs the surgeon that the drill head 108 and drill bit need to be rotated. Referring now to FIG. 8, the view illustrates the drill head 108 rotated so that the sidewalls $108_S$, $110_S$ are no longer visible. The drill head 108 is also properly positioned inside the targeting ring 112. The bit 110 is also located within the aiming ring 124 thus providing a clear visualization to the surgeon that the drill bit 110 is properly aligned with the planned trajectory for the planned implant hole.

Figure 8A:
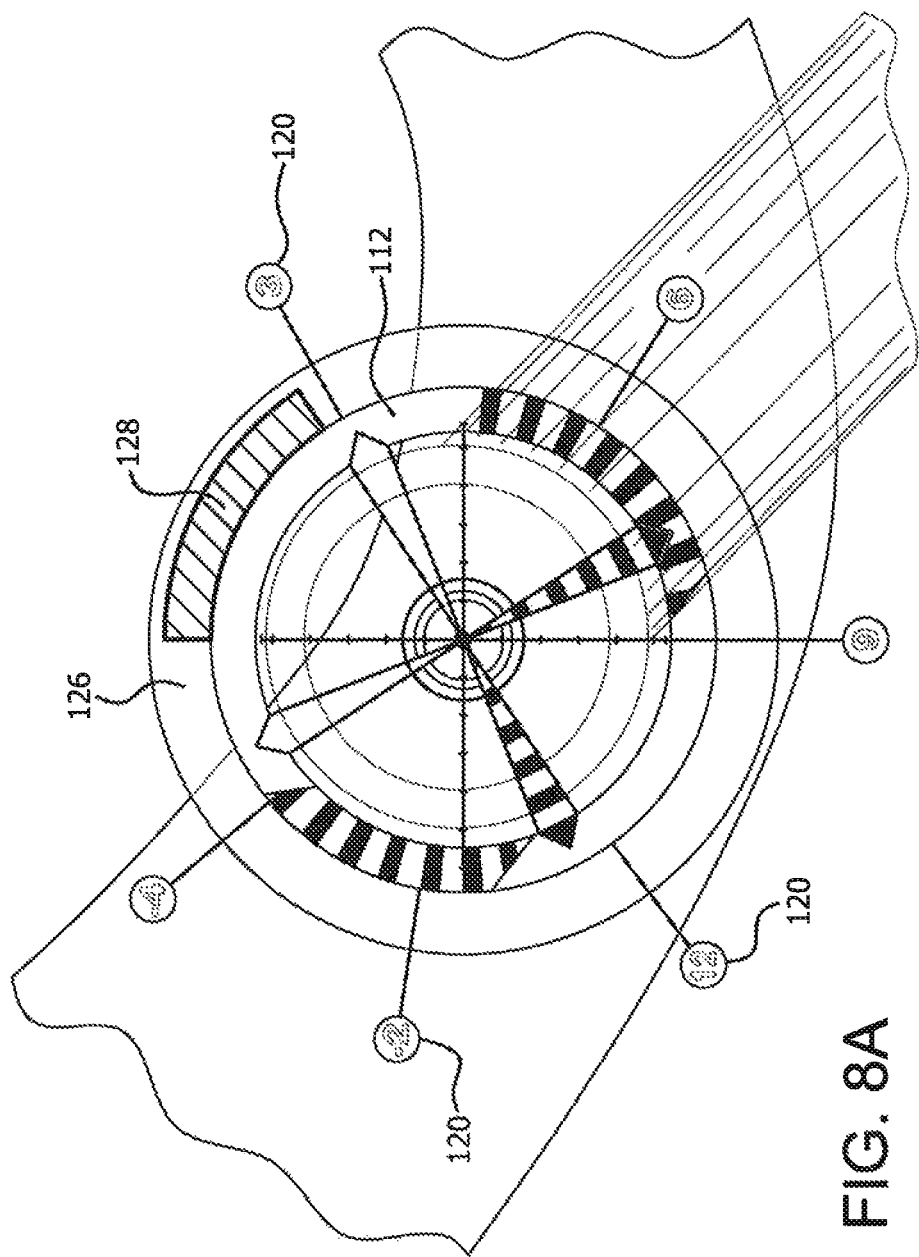
FIG. 8A illustrates the graphical interface of FIG. 8 depicting a change in depth of a drill tip along a planned drill hole.

Once appropriately aligned, the surgeon can begin drilling into the jaw. The desired depth into the bone is determined during preoperative planning and is part of the planned implant hole data 204 provided to the surgical guidance program 210. The present invention preferably provides a visual cue as part of the guidance indicator 102 that informs the surgeon on the depth. Referring to FIG. 8, a depth indicator 126 is preferably depicted as a ring around the outside of and concentric with the targeting ring. FIG. 8 illustrates the depth indicator 126 prior to drilling into the bone. The depth indicator 126 is preferably unfilled or lightly shaded so as to also be translucent. Once drilling begins and the tip of the drill bit begins to enter the bone, the program 210 begins to fill the depth indicator 126, preferably with an initial color or shading 128, such as yellow, in real time as the depth increases into the bone. See, FIGS. 8A and 8B. This provides visual guidance to the surgeon as to how far into the bone the drill has progressed. The numeric depth markers 120 positioned circumferentially about the depth indicator 126, show the depth into the bone that the drill has progressed. The system can be programmed such that the scale numbering and/or the units used can be changed during the planning stage. For example, in the illustrated embodiment, each numerical depth marker 120 indicates 3 mm in depth into the bone up to 12 mm. For a planned hole that is not as deep, each numeric depth marker 120 may only represent 1 mm in drilled depth. The planned desired depth is preferably shown on the depth indicator (in the illustrated embodiment, it is 12 mm). To anticipate over-drilling, the depth indicator 126 may also include additional numeric depth markers that are depicted in a different color and that may indicate the depth past the planned depth, e.g., −2 mm. The numeric depth markers 120 can either be regularly spaced or may correlate to specific meaningful measurements. For example, an implant hole is typically not drilled using a single size drill bit 110. Instead, successively larger bits are used. The marks on the depth indicator can therefore represent the depth each drill bit 110 should be inserted. The sequence of drill bits 110 and associated depths can be preoperatively set by the surgeon at the time of planning or the sequence may be determined from a database that correlates a selected implant model with the surgical tool sequence.

Figure 8B:
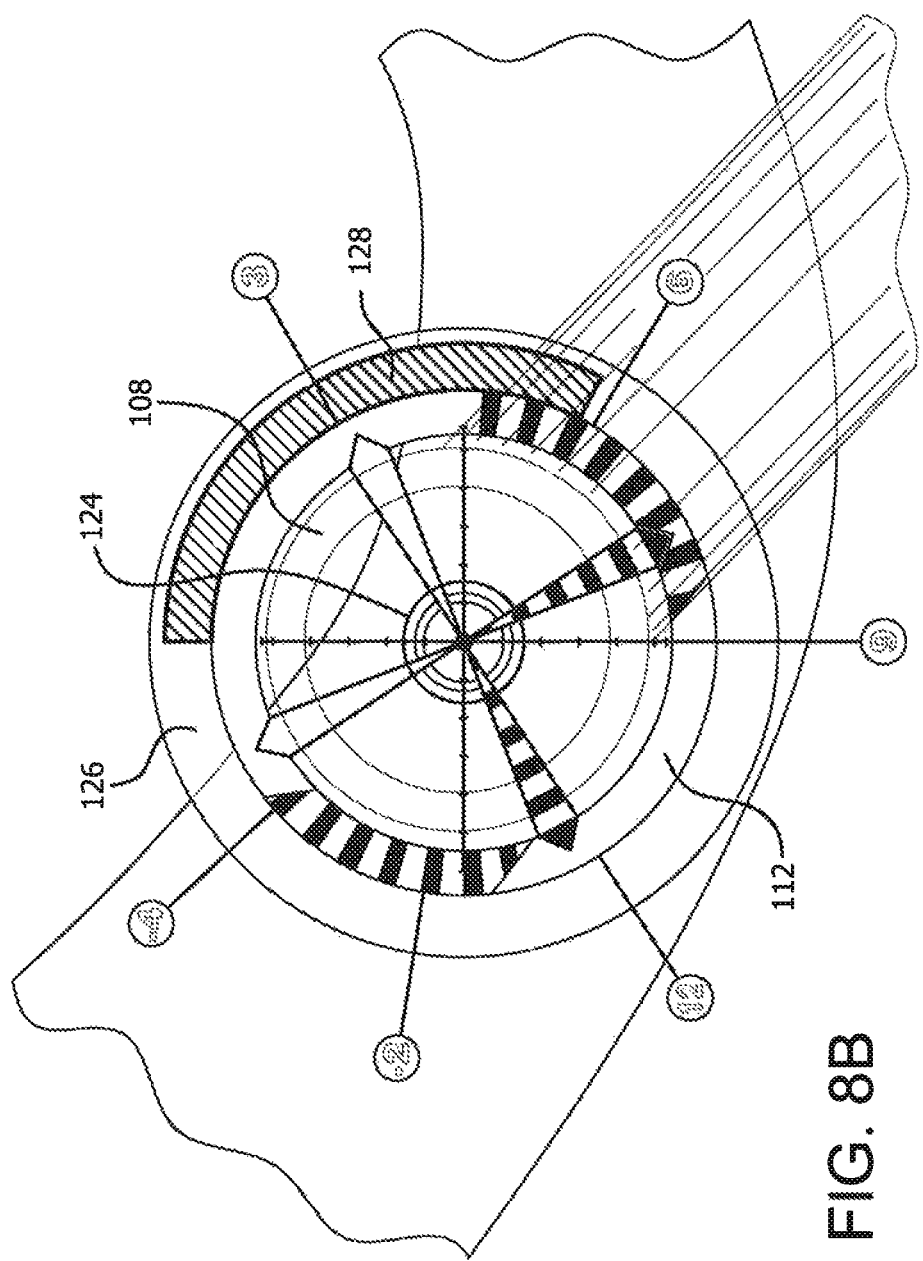
FIG. 8B illustrates the graphical interface of FIG. 8 depicting a further change in depth of a drill tip along the planned drill hole.
Figure 8C:
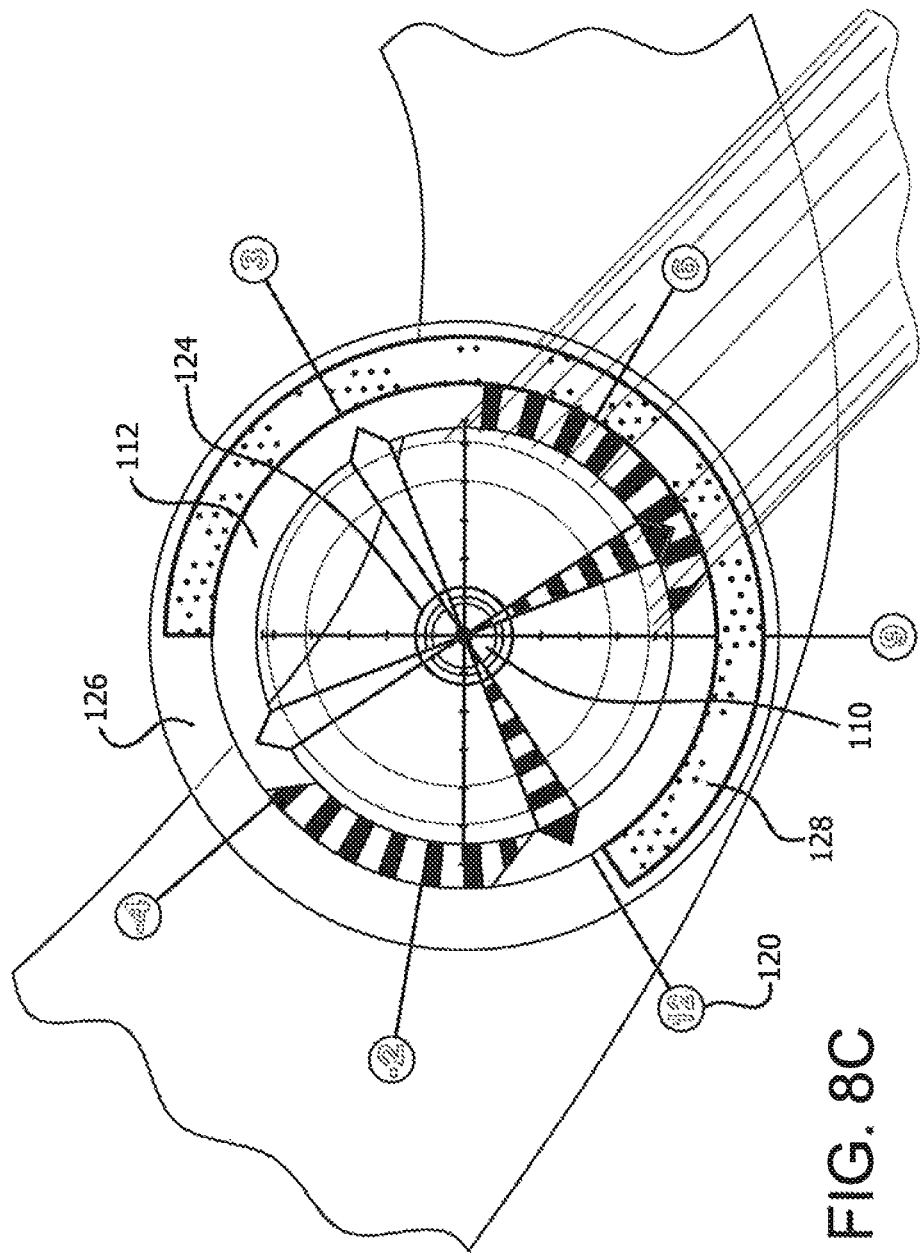
FIG. 8C illustrates the graphical interface of FIG. 8 depicting the drill tip reaching the desired drilling depth.
Figure 8D:
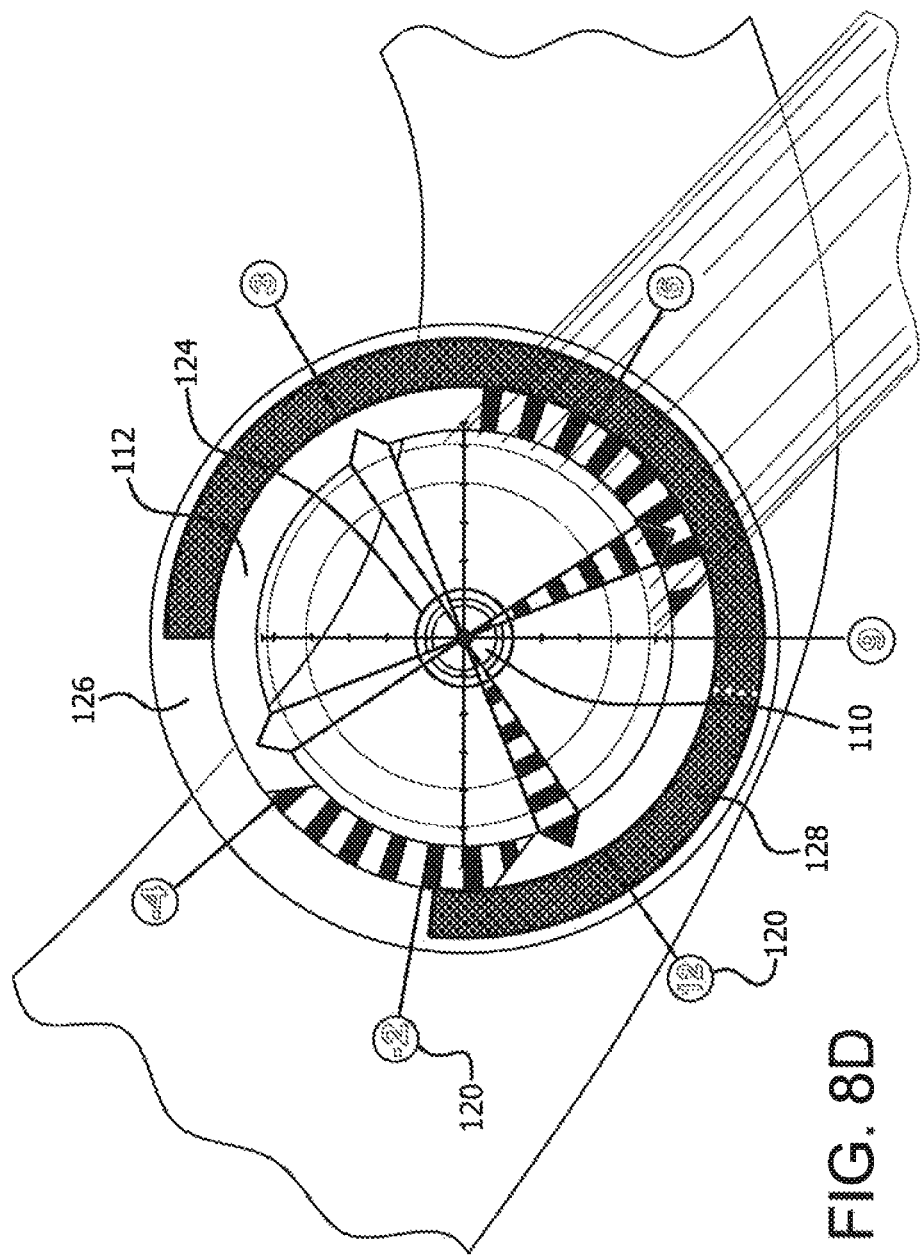
FIG. 8D illustrates the graphical interface of FIG. 8 depicting a the drill tip exceeding the desired drilling depth.

FIG. 8B depicts how a change in the drill bit diameter by a surgeon can affect the guidance indicator. In this embodiment, a smaller drill bit 110 was attached to the drill 104. As such, the aiming ring 124 is preferably automatically updated to a smaller diameter that correlates to the diameter of the smaller drill bit 110. The depth indicator 126 is shown with additional shading or coloring 128 to depict the current depth. As the drilling progresses, the coloring of the depth indicator 126 preferably changes to highlight to the surgeon where the depth is compared to the planned drilling depth. For example, the color may progress in the order: yellow (keep advancing) (slanted hatching in FIG. 8B), green (the drill is at the pre-planned depth) (dotted shading in FIG. 8C), and red (the drilling has gone too deep) (heavy shading in FIG. 8D). Of course other coloring or shading may be used. Audible indictors may also be provided, such as an alarm when the planned depth is exceeded. It is also contemplated that an audible signal or verbal signal can be provided at predetermined depths of the drill tip into the bone.

Figure 9:
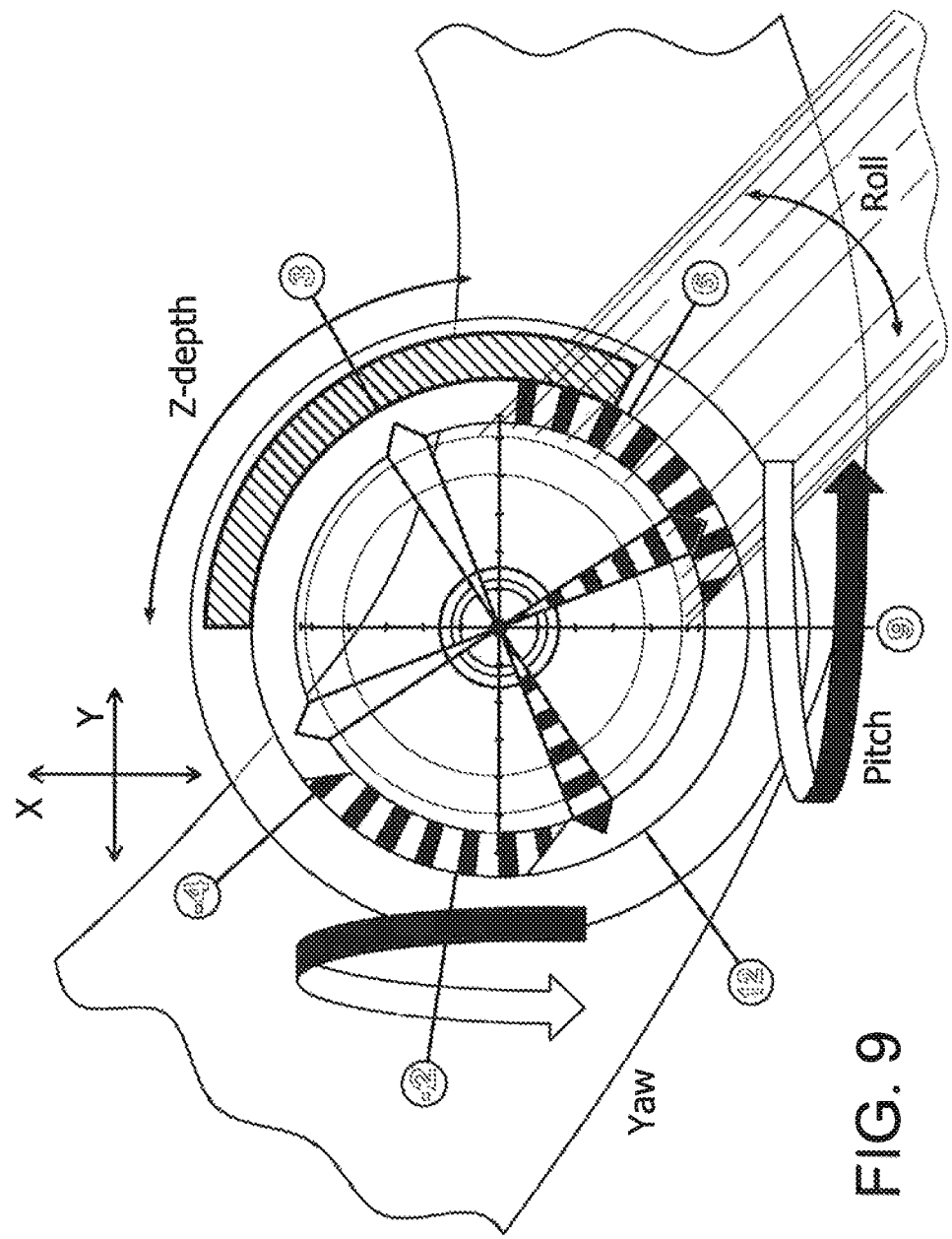
FIG. 9 illustrates the different degrees of freedom provided with the graphical interface of FIG. 8.

As shown in FIG. 9, the present invention provides six degrees of positional/directional freedom depicted in a single view. The X/Y coordinates show the position in the plane in which the image is formed. The orthogonal Z direction is depicted by the depth indicator. The orientation/angulation of the drill 104 is given by the alignment of the hollowed-out drill head 108 within the view. The pitch and yaw visible in this view depict the correct angulation of the drill with respect to the planned drill path. The roll of the drill around the drill axis gives the user an orientation of the drill with respect to the body itself so that the drill head 108 is not floating in space. This helps to quickly convey to the surgeon how to correct the orientation/location of the drill. As should be apparent from the above discussion, the present invention is tracking the x, y, z pitch and roll of the tool. However, in the context of the display, the image depicted is the x, y, pitch and roll and yaw of the surgical tool in the view. The depth of the tool is the depicted by the depth indicator (either visually or audibly).

In one embodiment, the system 200 permits the surrounding operating area (e.g., the bone) to be modified to make it more transparent and depict obstacles within the scene, such as nerves. The distance to the nerves along the implant trajectory can be added on the wrap-around depth indicator by the software in the based on a known distance, or could be added based on the current projected trajectory of the drill bit 110 and a known or detected location of the nerve. This can all be done in an automated fashion. Any conventional method for detecting nerves in CT scans or in a patient can be used.

The system 200 may also be configured to change the colors or shading of various cues of the guidance indicator 102, e.g., the reticle or the inner aiming ring, when the physician is too far from the correct planned drilling angle.

It should be apparent that the wrap-around depth indicator 126 is only one embodiment for visually depicting the depth of the drill bit. For example, the view could be modified such that there is a visual indicator that resizes to show depth. For instance, the aiming ring 124 could start large and shrink to the diameter of the drill bit at the correct depth. Alternately, the targeting ring can be adjusted to get smaller as the depth advances until the targeting ring overlies the aiming ring, thus indicating that the desired depth has been achieved.

Any of the visual components that are displayed could be rendered with different lighting, shading, color, and fill effects within the scope of the present invention.

Some of the unique features of the invention are a third-person oriented, realistic view of the surgical area, including a graphical representation of the drill and the jaw in the display rendered as how they generally appear provide the user with a sense that the display is a real-life depiction, which makes the user feel more comfortable that what they are seeing is happening live. Also, providing these objects in the specific orientation of looking down on the implant hole's longitudinal axis is unique. The system provides a view outside of the surgical area at the point where the tip of the drill bit is located. The system also preferably depicts the drill, drill bit, jaw, nerves and other components to scale, updated in real time and rendered in the an orthographic projection.

By including the depth indicator 126 as part of the guidance indicator 102 allows the surgeon to maintain attention on the target (the planned implant hole) without the need to shift focus to determine the drill's current depth.

The system or systems described herein may be implemented on any form of computer or computers. The system of the present invention may include a software program stored on a computer and/or storage device (e.g., mediums), and/or may be executed through a network. The method may be implemented through program code or program modules stored on a storage medium.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail.

Finally, the use of any and all examples, or exemplary language (e.g., "such as") provided herein, is intended merely to better illuminate the invention and does not pose a limitation on the scope of the invention unless otherwise claimed. Numerous modifications and adaptations will be readily apparent to those skilled in this art without departing from the spirit and scope of the invention.

What is claimed:

1. An image-guided system for a surgical procedure comprising:
    an image display apparatus for displaying a derived image of a surgical procedure;
    a detection system for detecting and tracking a position and orientation of an instrument and tracking the position and orientation of a portion of a patient, the detection system registering the position and orientation of the portion of the patient to a prestored three-dimensional image of a portion of the patient, the detection system determining the location and orientation of an operating axis of the instrument relative to the prestored three-dimensional image; and
    an image processing unit programmed to receive the prestored three-dimensional image, the instrument location and orientation, and a predetermined surgical plan including data representing a desired surgical result using the instrument for depiction on the prestored three-dimensional image and a planned trajectory to achieve the result,
    the image processing unit programmed to generate a derived image of the surgical procedure including a three-dimensional visual representation of a portion of the instrument on the prestored three-dimensional image based on the location and orientation of the operating axis relative to a longitudinal axis of the planned trajectory, and a depiction of the planned trajectory on the prestored three-dimensional image, the derived image being configured to be orthogonal to the planned trajectory,
    the image processing unit programmed to generate a graphical guidance indicator on the image display apparatus, the graphical guidance indicator oriented so as to be depicted orthogonal to the planned trajectory,
    the image processing unit programmed to send the derived image to the image display apparatus, the derived image and the graphical guidance indicator providing a visual depiction of at least five degrees of freedom of motion of the instrument relative to the surgical plan, and
    the image processing unit programmed to change the depiction of the graphical guidance indicator based on the movement of the instrument in accordance with the surgical plan.

2. The image-guided system according to claim 1, wherein the surgical result is a drilled hole with a final depth and wherein the surgical plan is a three-dimensional representation of the drilled hole, and wherein the system permits the selection of the three dimensional drilled hole shape from a set of prestored shapes.

3. The image-guided system according to claim 1, wherein the instrument is a drill with a drill bit, and the operating axis is a longitudinal axis of the drill bit, and wherein the surgical procedure is an oral surgical procedure which involves drilling into bone of a tooth.

4. The image-guided system according to claim 3, wherein the representation of the drill includes an annular cylindrical outer housing of a drill head and a concentric substantially cylindrical representation of a drill bit located within and spaced apart from the outer housing.

5. The image-guided system according to claim 4, wherein the planned trajectory includes a longitudinal axis and wherein the graphical guidance indicator includes an aiming ring disposed around and centered on the longitudinal axis of the planned trajectory, the aiming ring providing a visual guide for a surgeon to use to locate the representation of the drill bit on the longitudinal axis of the planned trajectory.

6. The image-guided system according to claim 5, wherein the graphical guidance indicator includes an X mark centered on the longitudinal axis of the planned trajectory, the orientation of the X mark being associated with the orientation of the prestored three-dimensional image.

7. The image-guided system according to claim 5, wherein the graphical guidance indicator includes a reticle centered on the longitudinal axis of the planned trajectory, the reticle providing a horizontal and vertical reference point relative to the image display.

8. The image-guided system according to claim 7, wherein the reticle includes spaced apart tick marks representing distance relative to the prestored three-dimensional image, and wherein the image processing unit is programmed to adjust the spacing of the tick marks on the image display depending on a zoom level of the display of the prestored three-dimensional image.

9. The image-guided system according to claim 5, wherein the graphical guidance indicator includes a targeting ring disposed around and centered on the longitudinal axis of the planned trajectory, the targeting ring being concentric with and located around the aiming ring, the targeting ring providing a visual guide for a surgeon to use to locate the representation of the drill head, so as to align the drill head with the longitudinal axis of the planned trajectory.

10. The image-guided system according to claim 9, wherein the image processing unit receives data representing the location of a nerve in the prestored three-dimensional image, the image processing unit programmed to depict a representation of the location of the nerve relative to the prestored three-dimensional image on the derived image.

11. The image-guided system according to claim 9, wherein the graphical guidance indicator includes a depth indicator adjacent to the targeting ring, the image processing unit programmed to visually change the depth indicator based on the movement of the drill bit along the planned trajectory.

12. The image-guided system according to claim 11, wherein the depth indicator is a portion of a ring having a center coincident with the center of the targeting ring, and wherein the image processing unit visually changes the depth indicator by depicting a larger portion of the ring correlated to the depth of the drill bit in relation to a planned drilling depth.

13. The image-guided system according to claim 11, wherein the image processing unit visually changes the shading or coloring of the depth indicator on the image display based on the depth of the drill bit in relation to a planned drilling depth.

14. The image-guided system according to claim 11, wherein the surgical plan involves using different diameter drill bits, and wherein the graphical guidance indicator visually changes to indicate when a different drill bit is required.

15. The image-guided system according to claim 14, wherein the aiming ring automatically resizes to a diameter to accommodate the new drill diameter.

16. The image-guided system according to claim 9, wherein the surgical result is a desired drilling depth, and wherein the image processing unit provides audible signals as the drill bit progresses along the planned trajectory toward the desired drilling depth.

17. The image-guided system according to claim 1, wherein the surgical result is a drilled hole with a depth and wherein the surgical plan is a three-dimensional representation of the drilled hole, wherein the instrument is a drill and the representation of the drill includes an annular cylindrical outer housing of a drill head and a concentric substantially cylindrical representation of a drill bit located within and spaced apart from the outer housing, wherein the graphical guidance indicator includes an aiming ring disposed around and centered on the planned trajectory, the aiming ring providing a visual guide for a surgeon to use to locate the representation of the drill bit on the planned trajectory, wherein the aiming ring is depicted with a shape corresponding to a shape of the three-dimensional hole taken orthogonal to a longitudinal axis of the three-dimensional hole.

18. A visual guidance system for use in a surgical procedure, the surgical procedure including data representing the movement of a surgical instrument and a surgical area of a patient, and a display for displaying movement of a representation of the surgical instrument on a prestored three-dimensional image of the surgical area, the guidance system comprising:
an image processing unit programmed to receive a prestored three-dimensional image of the surgical area, a detected location and orientation of an operating axis and a tip of an instrument being used in the surgical procedure, and a surgical plan including a planned trajectory that the tip and the operating axis should follow,
the image processing unit programmed to generate a derived representation of the surgical procedure using the prestored three-dimensional image and a digital representation of a portion of the instrument at a location on the prestored three-dimensional image related to the detected location and orientation of the operating axis and the tip,
the image processing unit programmed to generate a graphical guidance indicator on the prestored three-dimensional image with a center point of the graphical guidance indicator centered on the planned trajectory, the graphical guidance indicator being displayed orthogonal to the planned trajectory,
the image processing unit programmed to send the derived representation of the surgical procedure to the display, the derived image and the graphical guidance indicator providing a visual depiction of at least five degrees of freedom of motion of the instrument relative to the surgical plan, and
the image processing unit programmed to change the graphical guidance indicator based on the movement of the instrument in accordance with the surgical plan.

19. The image-guided system according to claim 18, wherein the surgical procedure is an oral surgical drilling procedure, wherein the instrument is a drill with a drill bit, the operating axis being the longitudinal axis of the drill bit and the tip being the tip of the drill bit, and wherein the surgical plan includes a depth that the tip of the drill bit is to reach during a portion of the surgical procedure.

20. The image-guided system according to claim 19, wherein the representation of the instrument includes an annular cylindrical outer housing representation of a drill head and a concentric substantially cylindrical representation of a drill bit located within and spaced apart from the outer housing.

21. The image-guided system according to claim 20, wherein the planned trajectory includes a longitudinal axis and wherein the graphical guidance indicator includes an aiming ring disposed around and centered on the longitudinal axis of the planned trajectory, the aiming ring providing a visual guide for a surgeon to use to locate the representation of the drill bit on the longitudinal axis of the planned trajectory.

22. The image-guided system according to claim 21, wherein the graphical guidance indicator includes an X mark centered on the longitudinal axis of the planned trajectory, the orientation of the X mark being associated with the orientation of the prestored three-dimensional image.

23. The image-guided system according to claim 21, wherein the graphical guidance indicator includes a reticle centered on the longitudinal axis of the planned trajectory, the reticle providing a horizontal and vertical reference point relative to the image display.

24. The image-guided system according to claim 23, wherein the reticle includes spaced apart tick marks representing distance relative to the prestored three-dimensional image, and wherein the image processing unit is programmed to adjust the spacing of the tick marks on the image display depending on a zoom level of the display of the prestored three-dimensional image.

25. The image-guided system according to claim 21, wherein the graphical guidance indicator includes a targeting ring disposed around and centered on the longitudinal axis of the planned trajectory, the targeting ring being concentric with and located around the aiming ring, the targeting ring providing a visual guide for a surgeon to use to locate the representation of the drill head, so as to align the drill head with the longitudinal axis of the planned trajectory.

26. The image-guided system according to claim 25, wherein the image processing unit receives data representing the location of a nerve in the prestored three-dimensional image, the image processing unit programmed to depict a representation of the location of the nerve relative to the prestored three-dimensional image on the derived image.

27. The image-guided system according to claim 25, wherein the graphical guidance indicator includes a depth indicator, the image processing unit programmed to visually change the depth indicator based on the movement of the tip of the drill bit along the planned trajectory and towards the planned depth.

28. The image-guided system according to claim 27, wherein the depth indicator is a portion of a ring having a center coincident with the center of the targeting ring, and wherein the image processing unit visually changes the depth indicator by depicting a larger portion of the ring correlated to the depth of the tip of the drill bit in relation to the planned depth.

29. The image-guided system according to claim 27, wherein the image processing unit visually changes the shading or coloring of the depth indicator on the image display based on the depth of the tip of the drill bit in relation to the planned depth.

30. The image-guided system according to claim 27, wherein the surgical plan involves using different diameter drill bits, and wherein the graphical guidance indicator visually changes to indicate when a different drill bit is required.

31. The image-guided system according to claim 25, wherein the image processing unit provides audible signals as the tip of the drill bit progresses along the planned trajectory toward the planned depth.

32. The image-guided system according to claim 18, wherein the surgical result is a drilled hole with a depth and wherein the surgical plan is a three-dimensional representation of the drilled hole, wherein the instrument is a drill and the representation of the drill includes an annular cylindrical outer housing of a drill head and a concentric substantially cylindrical representation of a drill bit located within and spaced apart from the outer housing, wherein the graphical guidance indicator includes an aiming ring disposed around and centered on the planned trajectory, the aiming ring providing a visual guide for a surgeon to use to locate the representation of the drill bit on the planned trajectory, wherein the aiming ring is depicted with a shape corresponding to a shape of the three-dimensional hole taken orthogonal to a longitudinal axis of the three-dimensional hole.

33. A method of providing visual guidance for a surgical instrument during a surgical procedure, the method providing the steps of:
providing an image-guided system according to claim 1;
retrieving a prestored three-dimensional image of the surgical area;
retrieving a digital representation of a surgical instrument being using in the surgical procedure;
receiving actual location and orientation data for the surgical instrument;
depicting at least a portion of the digital surgical instrument on the prestored three-dimensional image at a location and orientation that is based upon the actual location and orientation data;
retrieving a surgical plan including a planned surgical trajectory that the instrument is to proceed along during the surgical procedure;
displaying the surgical plan on the prestored three-dimensional image;
displaying a graphical guidance indicator on the prestored three-dimensional image, the graphical guidance indicator being displayed orthogonal to the planned trajectory with a point that is centered on the planned trajectory, the combination of the depiction of the digital surgical instrument and the graphical guidance indicator providing a visual depiction of at least five degrees of freedom of motion of the digital surgical instrument relative to the surgical plan, and
updating the display of the graphical guidance indicator and the digital surgical instrument based on the actual movement of the instrument.

34. The method of providing visual guidance according to claim 33, wherein prior to the step of depicting at least a portion of the digital surgical instrument, the method involves the step of sending the prestored three-dimensional image to a display.

35. The method of providing visual guidance according to claim 33, wherein the instrument is a drill with a drill bit, and wherein the procedure is an oral surgical procedure which involves drilling into bone of a tooth, and wherein the step of depicting at least a portion of the digital surgical instrument involves displaying an annular cylindrical outer housing representative of a drill head and displaying a concentric substantially cylindrical representation of a drill bit located within and spaced apart from the outer housing.

36. A method of providing visual guidance according to claim 35, wherein the displaying of the graphical guidance indicator includes displaying an aiming ring disposed around and centered on the planned trajectory, the aiming ring providing a visual guide for a surgeon to use to locate the representation of the drill bit on the planned trajectory.

37. A method of providing visual guidance according to claim 36, wherein the displaying of the graphical guidance indicator includes displaying an X mark centered on the planned trajectory, the X mark being associated with the prestored three-dimensional image such that rotation of the prestored three-dimension image about the planned trajectory produces rotation of the X-mark about the planned trajectory.

38. A method of providing visual guidance according to claim 36, wherein the displaying of the graphical guidance indicator includes displaying a reticle centered on the planned trajectory, the reticle providing a horizontal and vertical reference point relative to the display.

39. A method of providing visual guidance according to claim 38, wherein the reticle includes spaced apart tick marks representing distance relative to the prestored three-dimensional image, and wherein method involves adjusting the spacing of the tick marks on the display depending on a zoom level of the prestored three-dimensional image on the display.

40. A method of providing visual guidance according to claim 36, wherein the displaying of the graphical guidance indicator includes displaying a targeting ring disposed around and centered on the planned trajectory, the targeting ring being concentric with and located around the aiming ring, the targeting ring providing a visual guide for a surgeon to use to locate the representation of the drill head so as to align the drill head with the planned trajectory.

41. A method of providing visual guidance according to claim 40, further comprising the step of receiving data representing the location of a nerve, depicting a representation of the location of the nerve on the prestored three-dimensional image based on the location of the nerve.

42. A method of providing visual guidance according to claim 40, wherein the displaying of the graphical guidance indicator includes displaying a depth indicator adjacent to the targeting ring, and wherein the method involves the step of changing the depth indicator based on the movement of the drill bit along the planned trajectory.

43. A method of providing visual guidance according to claim 42, wherein the depth indicator is a portion of a ring having a center coincident with the center of the targeting ring, and wherein the step of changing the depth indicator involves depicting a larger portion of the ring correlated to the depth of the drill bit in relation to a planned drilling depth.

44. A method of providing visual guidance according to claim 43, wherein the step of changing the depth indicator involves changing the shading or coloring of the depth indicator on the display based on the depth of the drill bit in relation to a planned drilling depth.

45. A method of providing visual guidance according to claim 43, wherein the surgical plan involves using different diameter drill bits, and wherein the method involves changing the graphical guidance indicator to indicate when a different drill bit is required.

46. A method of providing visual guidance according to claim 45, wherein the method involves changing the diameter of the aiming ring in relation to changes in the drill bit.

47. A method of providing visual guidance according to claim 40, wherein the surgical result is a desired drilling depth, and wherein the method involves providing audible signals as the drill bit progresses along the planned trajectory toward the desired drilling depth.

48. A method of providing visual guidance according to claim 33, wherein the surgical result is a drilled hole with a depth and wherein the surgical plan is a three-dimensional representation of the drilled hole, and wherein the step of depicting at least a portion of the digital surgical instrument involves displaying an annular cylindrical outer housing representative of a drill head and displaying a concentric substantially cylindrical representation of a drill bit located within and spaced apart from the outer housing, wherein the displaying of the graphical guidance indicator includes displaying an aiming ring disposed around and centered on the planned trajectory, the aiming ring providing a visual guide for a surgeon to use to locate the representation of the drill bit on the planned trajectory, wherein the aiming ring is depicted with a shape corresponding to a shape of the three-dimensional hole taken orthogonal to a longitudinal axis of the three-dimensional hole.

* * * * *